(12) United States Patent
Hogan et al.

(10) Patent No.: US 6,326,486 B1
(45) Date of Patent: Dec. 4, 2001

(54) POLYNUCLEOTIDE PROBES FOR DETECTION AND QUANTITATION OF BACTERIA IN THE FAMILY ENTEROBACTERIACEAE

(75) Inventors: James J. Hogan, Coronado; Patricia Gordon, San Diego, both of CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 09/565,156

(22) Filed: May 3, 2000

Related U.S. Application Data
(60) Provisional application No. 60/132,410, filed on May 3, 1999.

(51) Int. Cl.[7] ............................. C07H 21/04; C12Q 1/68
(52) U.S. Cl. ...................... 536/24.32; 536/23.7; 435/6
(58) Field of Search ................. 435/6, 810, 23.7; 536/24.32, 23.7

(56) References Cited

U.S. PATENT DOCUMENTS

| | | | |
|---|---|---|---|
| 4,851,330 | 7/1989 | Kohne | 435/6 |
| 5,030,557 | 7/1991 | Hogan et al. | 435/6 |
| 5,185,439 | 2/1993 | Arnold, Jr. et al. | 536/24.3 |
| 5,283,174 | 2/1994 | Arnold, Jr. et al. | 435/6 |
| 5,364,763 | 11/1994 | Kacian | 435/7.32 |
| 5,374,522 | 12/1994 | Murphy et al. | 435/6 |
| 5,514,551 | * 5/1996 | Yang et al. | 435/6 |
| 5,539,082 | 7/1996 | Nielsen et al. | 530/300 |
| 5,541,308 | 7/1996 | Hogan et al. | 536/23.1 |
| 5,591,578 | 1/1997 | Meade et al. | 435/6 |
| 5,627,275 | 5/1997 | Roll | 536/23.7 |
| 5,635,348 | 6/1997 | Leong | 435/6 |
| 5,656,207 | 8/1997 | Woodhead et al. | 252/700 |
| 5,681,698 | 10/1997 | Hogan et al. | 435/6 |
| 5,708,160 | 1/1998 | Goh et al. | 536/24.32 |
| 5,770,369 | 6/1998 | Meade et al. | 435/6 |
| 5,786,167 | 7/1998 | Tuompo et al. | 435/34 |
| 5,824,518 | 10/1998 | Kacian et al. | 435/91.21 |
| 5,837,452 | 11/1998 | Clark et al. | 435/6 |
| 5,840,488 | 11/1998 | Hogan | 435/6 |
| 5,849,497 | 12/1998 | Steinman | 435/6 |
| 5,945,286 | 8/1999 | Krihak et al. | 435/6 |
| 5,998,135 | 12/1999 | Rabbani et al. | 435/6 |
| 6,031,091 | 2/2000 | Arnold, Jr. et al. | 536/25.34 |

FOREIGN PATENT DOCUMENTS

| | | |
|---|---|---|
| 9820162 | 5/1998 | (WO) . |
| 9857158 | 12/1998 | (WO) . |
| 9857159 | 12/1998 | (WO) . |
| 9938612 | 8/1999 | (WO) . |
| 9958713 | 11/1999 | (WO) . |

OTHER PUBLICATIONS

Mittelman, M.W. et al. J. Microbiol. Methods 30:153–160 (1997).*
Berg, K.L. et al. J. Bacteriol. 169(4):1691–1701 (Apr. 1987).*
Derwent Publication Ltd., London, GB, An 1993–171846, "Oligonucleotide Probe Used for The Detection of Microbes", & JP 05 103700 A (NEC Corp.), Apr. 27, 1993, Abstract XP002156224, 1pg.
Minagawa H., "Oligonucleotide Probe and Detection of Bacterium with the Same",Abstract XP00215561, 1 pg., Oct. 1997.
Yoshiharu S., "Method for Specfying DNA Base Sequence", Abstract XP002155682, 1 pg. Oct. 1997.
Loge, F.J. et al. Water Environ. Res. 71(1):75–83, Jan.–Feb., 1999.*
Ahern, H. The Scientist 9(15):20., Jul. 1995.*
Arnold et al., "Assay Formats Involving Arcidinium–Ester–Labled DNA Probes", Clin. Chem., 35 (8):1588–1594 (1989).
Barone et al., "In situ activation of bis–dialkylaminophosphines–a new method for synthesizing deoxyoligonucleotides on polymer supports", Nuc. Acids. Res., 12(10):4051–4061 (1984).
Farmer, III, "Enterbacteriacae: Introduction and Indentification", Manual of Clin. Microbiol., 6th Ed., P.R. Murray et al., eds., chpt. 32:438–449 (1995).
Lane et al., "Rapid determination of 16S ribosomal RNA sequences for phylogenetic analyses", Proc. Natl. Acad. Sci. USA, 82:6955–6959 (1985).
Sambrook et al., Molecular Cloning—A Laboratory Manual, 2nd Ed., vol.2, Chpt. 9, "Analysis and Cloning of Eukaryotic Genomic DNA"; Chpt. 10, "Preparation of Radiolabled DNA and RNA Probes"; and Chpt. 11, "Synthetic Oligonucleotide Probes".

* cited by examiner

Primary Examiner—Carla J. Myers
Assistant Examiner—Diana Johannson
(74) Attorney, Agent, or Firm—Michael J. Gilly

(57) ABSTRACT

Polynucleotides useful for specifically detecting bacteria in the family Enterobacteriaceae. Probes and accessory "helper oligonucleotides" are disclosed for use in hybridizing the rRNA and rDNA of Enterobacteriaceae without substantially cross-hybridizing with the rRNA or rDNA of numerous other bacterial and fungal species.

9 Claims, 1 Drawing Sheet

ENTERIC

E.coli
SEQ ID NO: 11    CAGGGCUACACACGUGCUACAAUGGCGCAUACAAAGAGAAGCGACCUCGCGAGAGCAAGCGGACCUCAUAAAGUGCGUCGUAGUCCGGAUUGG

K.pneumoniae
SEQ ID NO: 12    CAGGGCUACACACGUGCUACAAUGGCGCAUACAAAGAGAAGCGACCUCGCGAGAGCAAGCGGACCUCAUAAAGUAUGUCGUAGUCCGAUUGG

S.typhimurium
SEQ ID NO: 13    CAGGGCUACACACGUGCUACAAUGGCGCAUACAAAGAGAAGCGACCUCGCGAGAGCAAGCGGACCUCAUAAAGUGCGUCGUAGUCCGGAUUGG

C.diversus
SEQ ID NO: 14    CAGGGCUACACACGUGCUACAAUGGCGCAUAUACAAAGAGAAGCGACCUCGCGAGAGCAAGCGGACCUCAUAAAGUAUGUCGUAGUCCGAUUGG

C.freundii
SEQ ID NO: 15    UAGGGCUACACACGUGCUACAAUGGCGCAUACAAAGAGAAGCGACCUCGCGAGAGCAAGCGGACCUCAUAAAGUGCGUCGUAGUCCGGAUUGG

P.mirabilis
SEQ ID NO: 16    UAGGGCUACACACGUGCUACAAUGGCAGAUACAAAGAGAAGCGACCUCGCGAGAGCAAGCGGAACUCCAUAAAGUCUGUCGUAGUCCGAUUGG

H.alvei
SEQ ID NO: 17    UAGGGCUACACACGUGCUACAAUGGCGCAUACAAAGAGAAGCGACCUCGCGAGAGCAAGCGGACCUCAUAAAGUAUGUCGUAGUCCGAUUGG

Y.enterocolitica
SEQ ID NO: 18    UAGGGCUACACACGUGCUACAAUGGCAGAUACAAAGUGAAGCGAACUCGCGAGAGCAAGCGGACCACAUAAAGUCUGUCGUAGUCCGGAUUGG

OMeEntA1280(-)
SEQ ID NO: 3                                                                              (3')UGGAGUAUUCACGCAGCAUCAGG(5')

EntA1222(-)
SEQ ID NO: 2                                   (3')CGATGTGTGCACGATGTTACCGCGTATGTTTCTCTTCGCTG(5')

EntA1263(-)
SEQ ID NO: 1                                                          (3')GAGCGCTCTCGTTCGCC(5')

NON-ENTERIC

Campylobacter jejuni
SEQ ID NO: 19    CAGGGCGACACACGUGCUACAAUGGCUAUACAAGAGACGCAAUACCGCGAGGUGGAGAAAAUCU-AUAAAUAUGUCCAGUUCGGAUUGU

L.pneumophila
SEQ ID NO: 20    UAGGGCUACACACGUGCUACAAUGGCCGAUACAGAGGGCGGCAAGCCCGCGAGGGGGAGCAAUCCUAAAAGUCGGAUCGGUAGUCCGGAUUGG

P.aeruginosa.crw
SEQ ID NO: 21    -AGGGCUACACACGUGCUACAAUGGUCGGUACAAGGGUUGCGAAGCCGCGAGGUGGAGCUAAUCCGCGAAAAACCGAUCGUAGUCCGAUCGG

E.faecalis
SEQ ID NO: 22    CUGGGCUACACACGUGCUACAAUGGGAAGUACAACGAGUCGCUAGACCGCGAGGUCGAGCAAUCUCUAAAGCUUCUCUCAGUUCGGAUUGC

FIG. 1

SEQUENCE LISTING

```
<160> NUMBER OF SEQ ID NOS: 23

<210> SEQ ID NO 1
<211> LENGTH: 17
<212> TYPE: DNA
<213> ORGANISM: Enterobacteriaceae

<400> SEQUENCE: 1
ccgcttgctc tcgcgag                                                  17

<210> SEQ ID NO 2
<211> LENGTH: 41
<212> TYPE: DNA
<213> ORGANISM: Enterobacteriaceae

<400> SEQUENCE: 2
gtcgcttctc tttgtatgcg ccattgtagc acgtgtgtag c                       41

<210> SEQ ID NO 3
<211> LENGTH: 24
<212> TYPE: RNA
<213> ORGANISM: Enterobacteriaceae

<400> SEQUENCE: 3
ggacuacgac gcacuuuaug aggu                                          24

<210> SEQ ID NO 4
<211> LENGTH: 16
```

-continued

```
<212> TYPE: RNA
<213> ORGANISM: Pan-bacterial

<400> SEQUENCE: 4
cgacaaggaa uuucgc                                                  16

<210> SEQ ID NO 5
<211> LENGTH: 17
<212> TYPE: RNA
<213> ORGANISM: Pan-bacterial

<400> SEQUENCE: 5
uaccuuagga ccguuau                                                 17

<210> SEQ ID NO 6
<211> LENGTH: 16
<212> TYPE: RNA
<213> ORGANISM: Pan-bacterial

<400> SEQUENCE: 6
caggucggaa cuuacc                                                  16

<210> SEQ ID NO 7
<211> LENGTH: 22
<212> TYPE: DNA
<213> ORGANISM: Pan-fungal

<400> SEQUENCE: 7
gtctggacct ggtgagtttc cc                                           22

<210> SEQ ID NO 8
<211> LENGTH: 23
<212> TYPE: RNA
<213> ORGANISM: Pan-fungal

<400> SEQUENCE: 8
cguguugagu caaauuaagc cgc                                          23

<210> SEQ ID NO 9
<211> LENGTH: 26
<212> TYPE: DNA
<213> ORGANISM: Pan-fungal

<400> SEQUENCE: 9
gcucucaauc ugucaauccu uauugu                                       26

<210> SEQ ID NO 10
<211> LENGTH: 82
<212> TYPE: DNA
<213> ORGANISM: Enterobacteriaceae

<400> SEQUENCE: 10
ggactacgac gcactttatg aggtccgctt gctctcgcga ggtcgcttct ctttgtatgc   60
gccattgtag cacgtgtgta gc                                           82

<210> SEQ ID NO 11
<211> LENGTH: 93
<212> TYPE: RNA
<213> ORGANISM: E. coli

<400> SEQUENCE: 11
cagggcuaca cacgugcuac aauggcgcau acaaagagaa gcgaccucgc gagagcaagc   60
```

-continued ggaccucaua aagugcgucg uaguccggau ugg                          93

<210> SEQ ID NO 12
<211> LENGTH: 93
<212> TYPE: RNA
<213> ORGANISM: K. pneuminoae

<400> SEQUENCE: 12
cagggcuaca cacgugcuac aauggcauau acaaagagaa gcgaccucgc gagagcaagc    60
ggaccucaua aaguaugucg uaguccggau ugg                         93

<210> SEQ ID NO 13
<211> LENGTH: 93
<212> TYPE: RNA
<213> ORGANISM: S. typhimurium

<400> SEQUENCE: 13
cagggcuaca cacgugcuac aauggcgcau acaaagagaa gcgaccucgc gagagcaagc    60
ggaccucaua aagugcgucg uaguccggau ugg                         93

<210> SEQ ID NO 14
<211> LENGTH: 93
<212> TYPE: RNA
<213> ORGANISM: C. diversus

<400> SEQUENCE: 14
cagggcuaca cacgugcuac aauggcauau acaaagagaa gcgaccucgc gagagcaagc    60
ggaccucaua aaguaugucg uaguccggau ugg                         93

<210> SEQ ID NO 15
<211> LENGTH: 93
<212> TYPE: RNA
<213> ORGANISM: C. freundii

<400> SEQUENCE: 15
uagggcuaca cacgugcuac aauggcgcau acaaagagaa gcgaccucgc gagagcaagc    60
ggaccucaua aagugcgucg uaguccggau ugg                         93

<210> SEQ ID NO 16
<211> LENGTH: 93
<212> TYPE: RNA
<213> ORGANISM: P. mirabilis

<400> SEQUENCE: 16
uagggcuaca cacgugcuac aauggcagau acaaagagaa gcgaccucgc gagagcaagc    60
ggaacucaua aagucugucg uaguccggau ugg                         93

<210> SEQ ID NO 17
<211> LENGTH: 93
<212> TYPE: RNA
<213> ORGANISM: H. alvei

<400> SEQUENCE: 17
uagggcuaca cacgugcuac aauggcauau acaaagagaa gcgaacucgc gagagcaagc    60
ggaccucaua aaguaugucg uaguccggau ugg                         93

<210> SEQ ID NO 18
<211> LENGTH: 93
<212> TYPE: RNA
<213> ORGANISM: Y. enterocolitica -continued

```
<400> SEQUENCE: 18
uagggcuaca cacgugcuac aauggcagau acaaagugaa gcgaacucgc gagagcaagc      60
ggaccacaua aagucugucg uaguccggau ugg                                  93

<210> SEQ ID NO 19
<211> LENGTH: 92
<212> TYPE: RNA
<213> ORGANISM: Campylobacter jejuni

<400> SEQUENCE: 19
cagggcgaca cacgugcuac aauggcauau acaaugagac gcaauaccgc gagguggaga      60
aaaucuauaa aauauguccc aguucggauu gu                                   92

<210> SEQ ID NO 20
<211> LENGTH: 93
<212> TYPE: RNA
<213> ORGANISM: L. pneumophila

<400> SEQUENCE: 20
uagggcuaca cacgugcuac aauggccgau acagagggcg gcgaaggggc gaccuggagc      60
aaauccuuaa aagucggucg uaguccggau ugg                                  93

<210> SEQ ID NO 21
<211> LENGTH: 92
<212> TYPE: RNA
<213> ORGANISM: P. aeruginosa

<400> SEQUENCE: 21
agggcuacac acgugcuaca auggucggua caaagggguug cgaagccgcg agguggagcu     60
aaucccauaa aaccgaucgu aguccggauc gc                                   92

<210> SEQ ID NO 22
<211> LENGTH: 93
<212> TYPE: RNA
<213> ORGANISM: E faecalis

<400> SEQUENCE: 22
cugggcuaca cacgugcuac aauggaagu acaacgaguc gcuagaccgc gaggucaugc       60
aaaucucuua aagcuucucu caguucggau ugc                                  93

<210> SEQ ID NO 23
<211> LENGTH: 82
<212> TYPE: RNA
<213> ORGANISM: Enterobacteriaceae

<400> SEQUENCE: 23
gcuacacacg ugcuacaaug gcgcauacaa agagaagcga ccucgcgaga gcaagcggac      60
cucauaaagu gcgucguagu cc                                              82
```

POLYNUCLEOTIDE PROBES FOR DETECTION AND QUANTITATION OF BACTERIA IN THE FAMILY ENTEROBACTERIACEAE

RELATED APPLICATIONS

This application claims the benefit of U.S. Provisional Application No. 60/132,410, filed May 3, 1999. The disclosure of this related application is hereby incorporated by reference.

FIELD OF THE INVENTION

The present invention relates to nucleic acid detection systems. More specifically, the invention relates to polynucleotide probes having binding specificity for rRNA or rDNA of bacteria in the family Enterobacteriaceae.

BACKGROUND OF THE INVENTION

Enterobacteriaceae are Gram-negative, oxidase negative, rod-shaped bacteria that cause disease in a wide variety of animals. This family of bacteria, which includes approximately 29 genera, 107 named species and at least 50 unnamed species, is responsible for major economic losses in the veterinary and agricultural areas. Based on rRNA sequencing analysis, the Enterobacteriaceae have been placed in the Proteobacteria "subphyla" or "subdivision" of gamma, more particularly subgroup gamma-3. Significantly, bacteria in the family Enterobacteriaceae cause up to 50% of the nosocomial infections in the United States.

It is well established that two single strands of deoxyribonucleic acid ("DNA") or ribonucleic acid ("RNA") can associate or "hybridize" with one another to form a double-stranded structure having two strands held together by hydrogen bonds between complementary base pairs. The individual strands of nucleic acid are formed from nucleotides that comprise the bases: adenine (A), cytosine (C), thymidine (T), guanine (G), uracil (U) and inosine (I). In the double helical structure of nucleic acids, the base adenine hydrogen bonds with the base thymine or uracil, the base guanine hydrogen bonds with the base cytosine and the base inosine hydrogen bonds with adenine, cytosine or uracil. At any point along the chain, therefore, one may find the classical "Watson-Crick" base pairs A:T or A:U, T:A or U:A, and G:C or C:G. However, one may also find A:G, G:U and other "wobble" or mismatched base pairs in addition to the traditional ("canonical") base pairs.

A double-stranded nucleic acid hybrid will result if a first single-stranded polynucleotide is contacted under hybridization-promoting conditions with a second single-stranded polynucleotide having a sufficient number of contiguous bases complementary to the sequence of the first polynucleotide. DNA/DNA, RNA/DNA or RNA/RNA hybrids may be formed under appropriate conditions.

Generally, a probe is a single-stranded polynucleotide having some degree of complementarity with the nucleic acid sequence that is to be detected ("target sequence"). Probes commonly are labeled with a detectable moiety such as a radioisotope, an antigen or a chemiluminescent moiety.

Descriptions of nucleic acid hybridization as a procedure for detecting particular nucleic acid sequences are given by Kohne in U.S. Pat. No. 4,851,330, and by Hogan et al., in U.S. Pat. Nos. 5,541,308 and 5,681,698. These references also describe methods for determining the presence of RNA-containing organisms in a sample which might contain such organisms. These procedures require probes that are sufficiently complementary to the ribosomal RNA (rRNA) of one or more non-viral organisms or groups of non-viral organisms. According to the method, nucleic acids from a sample to be tested and an appropriate probe are first mixed and then incubated under specified hybridization conditions. Conventionally, but not necessarily, the probe will be labeled with a detectable label. The resulting hybridization reaction is then assayed to detect and quantitate the amount of labeled probe that has formed duplex structures in order to detect the presence of rRNA contained in the test sample.

With the exception of viruses, all prokaryotic organisms contain rRNA genes encoding homologs of the procaryotic 5S, 16S and 23S rRNA molecules. In eucaryotes, these rRNA molecules are the 5S rRNA, 5.8S rRNA, 18S rRNA and 28S rRNA which are substantially similar to the prokaryotic molecules. Probes for detecting specifically targeted rRNA subsequences in particular organisms or groups of organisms in a sample have been described previously. These highly specific probe sequences advantageously do not cross react with nucleic acids from any other bacterial species or infectious agent under appropriate stringency conditions.

The present invention provides polynucleotide probes that can be used to detect members of the family Enterobacteriaceae in a highly specific manner.

SUMMARY OF THE INVENTION

One aspect of the present invention relates to an oligonucleotide probe that specifically hybridizes a nucleic acid target region characteristic of bacteria in the family Enterobacteriaceae under a high stringency hybridization condition to form a detectable probe:target duplex. The invented oligonucleotide probe has a length of up to 100 nucleotides and includes at least 17 contiguous nucleotides contained within the sequence of SEQ ID NO:10 or the complement thereof. The high stringency hybridization conditions may be provided by either: (a) 0.48 M sodium phosphate buffer, 0.1% sodium dodecyl sulfate, and 1 mM each of EDTA and EGTA, or (b) 0.6 M LiCl, 1% lithium lauryl sulfate, 60 mM lithium succinate and 10 mM each of EDTA and EGTA. In certain embodiments the oligonucleotide probe is made of DNA. In other embodiments, the oligonucleotide probe includes at least one nucleotide analog. For example, the oligonucleotide probe may include at least one nucleotide analog having a methoxy group at the 2' position of a ribose moiety. In still other embodiments of the invention, the oligonucleotide probe has the sequence of any one of SEQ ID NO:1 or the complement thereof, SEQ ID NO:2 or the complement thereof, and SEQ ID NO:3 or the complement thereof. When the oligonucleotide has the sequence of either SEQ ID NO:2 or SEQ ID NO:3, the oligonucleotide is particularly useful as a helper oligonucleotide. Any of the disclosed oligonucleotides can include a detectable label which may be either a chemiluminescent label or a radiolabel. In a highly preferred embodiment, the oligonucleotide probe has the sequence given by SEQ ID NO:1. When this is the case, the oligonucleotide probe may further include a detectable label. This detectable label may be a chemiluminescent label, such as an acridinium ester.

Another aspect of the invention relates to a probe composition that can be used for detecting nucleic acids of bacteria in the family Enterobacteriaceae. This composition includes an oligonucleotide probe that hybridizes under a high stringency condition to an Enterobacteriaceae target region corresponding to E. coli rRNA nucleotide positions 1222–1303 to form a detectable probe:target duplex. The oligonucleotide probe has a length of up to 100 nucleotide bases and includes at least 17 contiguous nucleotides contained within the sequence of SEQ ID NO:10 or the complement thereof. Under the high stringency hybridization conditions the oligonucleotide probe specifically hybridizes nucleic acids that are present in *Citrobacter diversus, Citrobacter freundii, Enterobacter aerogenes, Enterobacter agglomerans, Enterobacter cloacae, Enterobacter fragilis, Enterobacter gergoviae, Escherichia coli, Escherichia fergusonii, Escherichia hermanii, Hafnia alvei, Klebsiella oxytoca, Klebsiella ozaenae, Klebsiella pneumoniae, Klebsiella rhinoscleromatis, Proteus mirabilis, Proteus penneri, Proteus vulgaris, Providencia alcalifaciens, Providencia rettgeri, Providencia stuartii, Salmonella enteritidis, Salmonella paratyphi, Salmonella typhi, Salmonella typhimurium, Serratia liquefaciens, Serratia marcescens, Shigella dysenteriae, Shigella sonnei, Yersinia enterocolitica, Yersinia intermedia* and *Yersinia pseudotuberculosis*. In certain embodiments the oligonucleotide probe is made of DNA. Examples of useful high stringency hybridization conditions include: (a) 0.48 M sodium phosphate buffer, 0.1% sodium dodecyl sulfate, and 1 mM each of EDTA and EGTA, and (b) 0.6 M LiCl, 1% lithium lauryl sulfate, 60 mM lithium succinate and 10 mM each of EDTA and EGTA. In a highly preferred embodiment, the oligonucleotide probe has the sequence of SEQ ID NO:1 or the complement thereof. Rather than having a length of 100 nucleotides, the invented oligonucleotide probe can have a length of up to 60 bases. For example, the oligonucleotide probe can have the length and sequence of SEQ ID NO:1. In general, the oligonucleotide probe may include a detectable label. This is true for oligonucleotides having lengths of from 17–100 nucleotides, or from 17–60 nucleotides in length, or even when the oligonucleotide probe has the length and sequence of SEQ ID NO:1. Regardless of the length of the labeled oligonucleotide, the detectable label may be either a chemiluminescent label or a radiolabel. In certain highly preferred embodiments, the chemiluminescent label is an acridinium ester. In other embodiments, regardless of the length of the oligonucleotide probe or whether the detectable label is a chemiluminescent label or a radiolabel, there can also be included in the composition at least one helper oligonucleotide that facilitates formation of the detectable probe:target duplex under the hybridization conditions. In these instances the helper oligonucleotide may include at least one nucleotide analog. For example, useful nucleotide analogs can include a ribose moiety having a methoxy group disposed at the 2' position. In highly preferred embodiments of the invented probe composition, the helper oligonucleotides may have the sequences of either SEQ ID NO:2 or SEQ ID NO:3.

Yet another aspect of the invention relates to a method for detecting the presence of bacteria in the family Enterobacteriaceae in a test sample. This method includes a step for providing to the test sample a probe composition that includes an oligonucleotide probe that hybridizes under a high stringency condition to an Enterobacteriaceae target region corresponding to *E. coli* rRNA nucleotide positions 1222–1303 to form a detectable probe:target duplex. The oligonucleotide probe has a length of up to 100 nucleotide bases and includes at least 17 contiguous nucleotides contained within the sequence of SEQ ID NO:10 or the complement thereof. Under the high stringency hybridization conditions the oligonucleotide probe specifically hybridizes nucleic acids present in *Citrobacter diversus, Citrobacter freundii, Enterobacter aerogenes, Enterobacter agglomerans, Enterobacter cloacae, Enterobacter fragilis, Enterobacter gergoviae, Escherichia coli, Escherichia fergusonii, Escherichia hermanii, Hafnia alvei, Klebsiella oxytoca, Klebsiella ozaenae, Klebsiella pneumoniae, Klebsiella rhinoscleromatis, Proteus mirabilis, Proteus penneri, Proteus vulgaris, Providencia alcalifaciens, Providencia rettgeri, Providencia stuartii, Salmonella enteritidis, Salmonella paratyphi, Salmonella typhi, Salmonella typhimurium, Serratia liquefaciens, Serratia marcescens, Shigella dysenteriae, Shigella sonnei, Yersinia enterocolitica, Yersinia intermedia* and *Yersinia pseudotuberculosis*. The invented method further includes a step for hybridizing under high stringency conditions any Enterobacteriaceae nucleic acid that may be present in the test sample with the probe composition to form a probe:target duplex. Finally, the method includes a step for detecting the probe:target duplex as an indicator of the presence of Enterobacteriaceae in the test sample. In one embodiment of the invented method there is a preliminary step for releasing nucleic acid from any bacteria that may be present in said test sample. According to another embodiment, the test sample is a lysate and so it is unnecessary to release nucleic acids from microorganisms or other cells. Examples of high stringency hybridization conditions that can be used in conjunction with the invented method include: (a) 0.48 M sodium phosphate buffer, 0. 1% sodium dodecyl sulfate, and 1 mM each of EDTA and EGTA, and (b) 0.6 M LiCl, 1% lithium lauryl sulfate, 60 mM lithium succinate and 10 mM each of EDTA and EGTA. In a highly preferred embodiment, the oligonucleotide probe used in the method has the length and sequence of SEQ ID NO:1. When this is the case, the oligonucleotide probe may include a detectable label, such as an acridinium ester. In that event, the detecting step may involve performing luminometry to detect any of the probe:target duplex. When the oligonucleotide probe has the length and sequence of SEQ ID NO:1, the probe composition may further include at least one helper oligonucleotide that facilitates formation of the probe:target duplex. Highly preferred helper oligonucleotides have the sequences of SEQ ID NO:2 and SEQ ID NO:3.

Still yet another aspect of the invention relates to a kit that can be used for detecting the presence of Enterobacteriaceae nucleic acids in a test sample. The kit includes a probe composition that includes an oligonucleotide probe that hybridizes under a high stringency condition to an Enterobacteriaceae target region corresponding to *E. coli* rRNA nucleotide positions 1222–1303 to form a detectable probe:target duplex. The oligonucleotide probe has a length of up to 100 nucleotide bases and includes at least 17 contiguous nucleotides contained within the sequence of SEQ ID NO:10 or the complement thereof. Under the high stringency hybridization conditions the oligonucleotide probe present in the kit specifically hybridizes nucleic acids present in *Citrobacter diversus, Citrobacter freundii, Enterobacter aerogenes, Enterobacter agglomerans, Enterobacter cloacae, Enterobacter fragilis, Enterobacter gergoviae, Escherichia coli, Escherichia fergusonii, Escherichia hermanii, Hafnia alvei, Klebsiella oxytoca, Klebsiella ozaenae, Klebsiella pneumoniae, Klebsiella rhinoscleromatis, Proteus mirabilis, Proteus penneri, Proteus vulgaris, Providencia alcalifaciens, Providencia rettgeri, Providencia stuartii, Salmonella enteritidis, Salmonella paratyphi, Salmonella typhi, Salmonella typhimurium, Serratia liquefaciens, Serratia marcescens, Shigella dysenteriae, Shigella sonnei, Yersinia enterocolitica, Yersinia intermedia* and *Yersinia pseudotuberculosis*. Also included in the kit are printed instructions specifying, in order of implementation, the steps to be followed for detecting said Enterobacteriaceae nucleic acid by detecting a complex between the oligonucleotide probe and an Enterobacteriaceae nucleic acid target. Both the probe composition and the printed instructions are in packaged combination with each other.

Definitions

As used herein, the following terms have the given meanings unless expressly stated to the contrary.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2-deoxyribose. For a 5'-nucleotide, the sugar contains a hydroxyl group (—OH) at the 5'-carbon-5. The term also includes analogs of such subunits, and particularly includes analogs having a methoxy group at the 2' position of the ribose (OMe). As used herein, methoxy oligonucleotides containing "T" residues have a methoxy group at the 2' position of the ribose moiety, and a uracil at the base position of the nucleotide.

A "non-nucleotide unit" is a unit which does not significantly participate in hybridization of a polymer. Such units must not, for example, participate in any significant hydrogen bonding with a nucleotide, and would exclude units having as a component one of the five nucleotide bases or analogs thereof.

An "oligonucleotide" is a nucleotide polymer having two or more nucleotide subunits covalently joined together. Oligonucleotides are generally about 10 to about 100 nucleotides in length. The sugar groups of the nucleotide subunits may be ribose, deoxyribose, or modified derivatives thereof such as OMe. The nucleotide subunits may by joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention.

A "target nucleic acid" is a nucleic acid comprising a target nucleic acid sequence.

A "target nucleic acid sequence," "target nucleotide sequence" or "target sequence" is a specific deoxyribonucleotide or ribonucleotide sequence that can be hybridized by an oligonucleotide.

An "oligonucleotide probe" is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promotor sequences, restriction endonuclease recognition sites, or sequences that confer a desired secondary or tertiary structure such as a catalytic active site can be used to facilitate detection using the invented probes. An oligonucleotide probe optionally may be labeled with a detectable moiety such as a radioisotope, a fluorescent moiety, a chemiluminescent moiety, an enzyme or a ligand, which can be used to detect or confirm probe hybridization to its target sequence. Oligonucleotide probes are preferred to be in the size range of from 10 to 100 nucleotides in length.

A "detectable moiety" is a molecule attached to, or synthesized as part of, a nucleic acid probe. This molecule should be uniquely detectable and will allow the probe to be detected as a result. These detectable moieties are often radioisotopes, chemiluminescent molecules, enzymes, haptens, or even unique oligonucleotide sequences.

A "hybrid" or a "duplex" is a complex formed between two single-stranded nucleic acid sequences by Watson-Crick base pairings or non-canonical base pairings between the complementary bases.

"Hybridization" is the process by which two complementary strands of nucleic acid combine to form a double-stranded structure ("hybrid" or "duplex").

"Complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or uracil (U), while guanine (G) ordinarily complements cytosine (C).

"Mismatch" refers to any pairing, in a hybrid, of two nucleotides which do not form canonical Watson-Crick hydrogen bonds. In addition, for the purposes of the following discussions, a mismatch can include an insertion or deletion in one strand of the hybrid which results in an unpaired nucleotide(s).

The term "stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid. Exemplary high stringency conditions are provided in the working Examples.

The term "probe specificity" refers to a characteristic of a probe which describes its ability to distinguish between target and non-target sequences.

The term "variable region" refers to a nucleotide polymer which differs by at least one base between the target organism and non-target organisms contained in a sample.

A "conserved region" is a nucleic acid subsequence which is not variable between at least two different polynucleotides.

"Bacteria" are members of the phylogenetic group eubacteria, which is considered one of the three primary kingdoms.

The term "sequence divergence" refers to a process by which nucleotide polymers become less similar during evolution.

The term "sequence convergence" refers to a process by which nucleotide polymers become more similar during evolution.

"Tm" refers to the temperature at which 50% of the probe is converted from the hybridized to the unhybridized form.

A "helper oligonucleotide" is an oligonucleotide that binds a region of a target nucleic acid other than the region that is bound by an oligonucleotide probe. Helper oligonucleotides impose new secondary and tertiary structures on the targeted region of the single-stranded nucleic acid so that the rate of binding of the oligonucleotide probe is accelerated. Although helper oligonucleotides are not labeled with a detectable label when used in conjunction with labeled oligonucleotide probes, they facilitate binding of labeled probes and so indirectly enhance hybridization signals.

The phrases "consist essentially of" or "consisting essentially of" means that the oligonucleotide has a nucleotide sequence substantially similar to a specified nucleotide sequence. Any additions or deletions are non-material variations of the specified nucleotide sequence which do not prevent the oligonucleotide from having its claimed property, such as being able to preferentially hybridize under high stringency hybridization conditions to its target nucleic acid over non-target nucleic acids.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from 100% to 80% or from 0 base mismatches in a 10 nucleotide target sequence to 2 bases mismatched in a 10 nucleotide target sequence. In preferred embodiments, the percentage is from 100% to 85%. In more preferred embodiments, this percentage is from 90% to 100%; in other preferred embodiments, this percentage is from 95% to 100%.

By "sufficiently complementary" or "substantially complementary" is meant nucleic acids having a sufficient amount of contiguous complementary nucleotides to form, under high stringency hybridization conditions, a hybrid that is stable for detection.

By "nucleic acid hybrid" or "probe:target duplex" is meant a structure that is a double-stranded, hydrogen-bonded structure, preferably 10 to 100 nucleotides in length, more preferably 14 to 50 nucleotides in length. The structure is sufficiently stable to be detected by means such as chemiluminescent or fluorescent light detection, autoradiography, electrochemical analysis or gel electrophoresis. Such hybrids include RNA:RNA, RNA:DNA, or DNA:DNA duplex molecules.

By "negative sense" is meant a nucleic acid molecule perfectly complementary to a reference (i.e., sense) nucleic acid molecule.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

By "preferentially hybridize" is meant that under high stringency hybridization conditions oligonucleotide probes can hybridize their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of bacteria in the family Enterobacteriaceae and distinguish their presence from that of other organisms. Preferential hybridization can be measured using techniques known in the art and described herein. For example, when compared with hybridization to *C. albicans* nucleic acids, oligonucleotide probes of the invention preferentially hybridize nucleic acids of bacteria in the family Enterobacteriaceae by about 50–7,000 fold.

An Enterobacteriaceae "target nucleic acid sequence region" refers to a nucleic acid sequence present in nucleic acid or a sequence complementary thereto found in bacteria of the family Enterobacteriaceae, which is not present in the nucleic acids of other species. Nucleic acids having nucleotide sequences complementary to a target sequence may be generated by target amplification techniques such as polymerase chain reaction (PCR) or transcription mediated amplification (e.g., Kacian and Fultz, Nucleic Acid Sequence Amplification Methods, U.S. Pat. No. 5,824,518).

BRIEF DESCRIPTION OF THE DRAWINGS

FIG. 1 shows an alignment of one oligonucleotide probe and two helper oligonucleotides with a collection of positively reactive and non-reactive target sequences.

DETAILED DESCRIPTION OF THE INVENTION

Herein we disclose preferred target nucleotide sequences for oligonucleotide probes and helper oligonucleotides that can be used to detect and identify rRNA or rDNA of bacteria within the family Enterobacteriaceae. Highly preferred polynucleotide probes and accessory helper oligonucleotides that are useful for specifically detecting these bacteria are particularly disclosed. The probes, which are complementary to particular rRNA sequences of the 16S rRNA, advantageously are capable of distinguishing Enterobacteriaceae from the known phylogenetically nearest neighbors.

In addition to having nucleic acid sequences that permit hybridization to the ribosomal RNA (rRNA) or DNA (rDNA) sequences of bacteria within the family Enterobacteriaceae, the oligonucleotide probes of the invention are at least 90% complementary, preferably perfectly complementary, to at least a portion of the target sequence region identified by SEQ ID NO:10. The portion is preferably at least 17 nucleotides in length, more preferably at least 24 nucleotides in length, and still more preferably at least 41 nucleotides in length.

As indicated above, the invented oligonucleotides are targeted to nucleic acid sequences of bacteria within the family Enterobacteriaceae. These oligonucleotides can be used as probes that preferentially hybridize to a nucleic acid target region of bacteria within the family Enterobacteriaceae to form a detectable duplex that indicates the presence of these bacteria. Alternatively, the invented oligonucleotides can be used as helper oligonucleotides that hybridize to a nucleic acid target region of bacteria within the family Enterobacteriaceae under high stringency hybridization conditions, and that can enhance the formation of a duplex between a labeled oligonucleotide probe and its complementary target nucleic acid.

In preferred embodiments, the oligonucleotide probes described herein selectively hybridize nucleic acids from bacteria within the family Enterobacteriaceae over those from other organisms under high stringency hybridization conditions. In some embodiments of the present invention, the oligonucleotide probe comprises a detectable moiety, such as an acridinium ester or a radioisotope.

Preferred methods for detecting the presence of bacteria within the family Enterobacteriaceae include the step of contacting a test sample under high stringency hybridization conditions with an oligonucleotide probe that preferentially hybridizes to a target nucleic acid sequence of bacteria within the family Enterobacteriaceae over a nucleic acid sequence of other organisms. The target ribosomal nucleic acid sequence contained in rRNA of bacteria in the family Enterobacteriaceae has the sequence given by SEQ ID NO:23. Prefered probes have sequences up to 100 nucleotides in length and have at least 17 contiguous nucleotides, more preferably 24 contiguous nucleotides, still more preferably 41 contiguous nucleotides contained in the sequence given by GGACTACGACGCACTTTATGAGGTCCGCTTGCTCTCGCGAGGTCGCTTCTCTTTGTATGCGCCATTGTAGCACGTGTGTAGC (SEQ ID NO:10). However, useful probes for hybridizing rDNA can be up to 100 nucleotides in length and have at least 17 contiguous nucleotides, more preferably 24 contiguous nucleotides, still more preferably 41 contiguous nucleotides contained in the sequence given by the complement of SEQ ID NO:10. The oligonucleotides may be RNA and DNA equivalents, and may contain nucleotide analogs.

Introduction and Background

In the development of the invention, rRNA sequences from a collection of related and unrelated organisms were aligned to identify conserved sequences in the 16S rRNA that could be used to distinguish the Enterobacteriaceae from other bacterial and eukaryotic organisms. The procedures employed to make this discovery included examination of partial or complete sequences of the rRNA or rDNA of multiple Enterobacteriaceae organisms and non-related phylogenetic neighbors, and aligning the sequences to reveal areas of maximum homology and examining the alignment for regions with sequence variation in order to identify rRNA sequences that are conserved among the members of the Enterobacteriaceae and that showed mismatches with the rRNAs of other genera. The sequences deduced as candidate probes according to the methods described below finally were tested against a panel of rRNA standards and bacterial lysates to verify their utility as probes under laboratory conditions.

Polynucleotide sequences of rRNAs are most conveniently determined using a dideoxynucleotide sequencing procedure. In this procedure, oligonucleotide primers of about 10–100 bases in length and complementary to conserved regions of rRNA from any of the 5S, 16S or 23S ribosome subunits can be extended by reverse transcriptase. The resulting DNA extension products can then be sequenced either by chemical degradation or by dideoxynucleotide sequencing (Lane et al., *Proc. Natl. Acad. Sci. USA* 82: 6955 (1985)). According to another preferred method, genomic sequences encoding the rRNA can also be determined.

The strong interdependence of secondary structure and function of the rRNA molecules is well known. Indeed, evolutionary changes in the primary sequence of the rRNA are effectively restricted such that secondary structure of the molecule will be maintained. For example, if a base is changed on one side of a helix of a rRNA molecule, then a compensating change will be made on the other side of the helix to preserve complementarity (this is referred to as covariance). This relationship allows two very different rRNA sequences to be "aligned" based on conserved primary sequence and conserved elements of the secondary structure. Once the sequences have been aligned, it becomes possible to identify conserved and variable regions of the rRNA sequence.

Variable regions of rRNAs were identified by comparative analysis using published rRNA sequences and sequences that were determined during the development of the present invention. Commercially available software can be used or adapted for the purposes disclosed herein. Since the sequence evolution at each of the variable regions (for example, spanning a minimum of 10 nucleotides) of rRNA is, for the most part, divergent and not convergent, we can confidently design probes based on a few rRNA sequences which differ between the target organism and its phylogenetically closest relatives. Indeed, we have detected sufficient variation between the rRNA sequences of numerous target organisms and their closest phylogenetic relatives in a single sample to permit the design of a probe that can be used according to the methods described below.

Probe Selection Guidelines

The following general guidelines can be used for designing probes having desirable characteristics in accordance with the present invention. Manipulation of one or more of the many factors that influence the extent and specificity of a hybridization reaction can determine the sensitivity and specificity of a particular probe. This is true whether or not the probe is perfectly complementary over the full length of its target polynucleotide sequence. Guidelines for preparing probes useful in connection with the invention now follow.

First, the stability of the probe:target nucleic acid hybrid should be chosen to be compatible with the assay conditions. This may be accomplished by avoiding long A and T rich sequences, by terminating the hybrids with G:C base pairs and by designing the probe in such a way that the Tm will be appropriate for standard conditions to be employed in the assay. The nucleotide sequence of the probe should be chosen so that the length and %G and %C result in a probe having a Tm about 2–10° C. higher than the temperature at which the final assay will be performed. The base composition of the probe is significant because G:C base pairs exhibit greater thermal stability when compared with A:T or A:U base pairs. Thus, hybrids involving complementary nucleic acids having a high G:C content will be stable at higher temperatures when compared with hybrids having a lower G:C content.

Ionic strength and temperature conditions at which a hybridization reaction will be conducted also should be considered when designing a probe having a negatively charged backbone, such as would be provided by phosphodiester linkages between nucleotides. It is generally known that hybridization rate increases as ionic strength of the reaction mixture increases. Similarly, the thermal stability of hybrids increases with increasing ionic strength. Conversely, hydrogen bond-disrupting reagents such as formamide, urea, DMSO and alcohols increase the stringency of hybridization. Destabilization of the hydrogen bonds by reagents in this class can greatly reduce the Tm. In general, optimal hybridization for synthetic oligonucleotide probes of about 10–50 bases in length occurs approximately 5° C. below the melting temperature for a given duplex. Hybridization reactions conducted below the temperature optimum may allow mismatched base sequences to hybridize, and can result in reduced probe specificity.

Second, the position at which the probe binds its target polynucleotide should be chosen to minimize the stability of hybrids formed between the probe and non-target polynucleotides. This may be accomplished by minimizing the length of perfect complementarity with polynucleotides of non-target organisms, by avoiding G:C rich regions of homology with non-target sequences, and by positioning the probe to span as many destabilizing mismatches as possible. Whether a probe sequence will be useful for detecting only a specific type of organism depends largely on thermal stability differences between probe:target hybrids and probe:non-target hybrids. The differences in Tm should be as large as possible to produce highly specific probes.

The length of the target nucleic acid sequence and the corresponding length of the probe sequence also are important factors to be considered when designing a probe useful for specifically detecting Enterobacteriaceae. While it is possible for polynucleotides that are not perfectly complementary to hybridize to each other, the longest stretch of perfectly homologous base sequence will ordinarily be the primary determinant of hybrid stability.

Third, regions of the rRNA which are known to form strong internal structures inhibitory to hybridization of a probe are less preferred as targets. Probes having extensive self-complementarity also should be avoided. As indicated above, hybridization is the association of two single strands of complementary nucleic acid to form a hydrogen bonded double-stranded structure. If one of the two strands is wholly or partially double-stranded, then it will be less able to participate in the formation of a new hybrid. Significantly, all rRNA molecules form very stable intramolecular hybrids.

The rate and extent of hybridization between a probe and its target can be increased substantially by designing the probe such that a substantial portion of the sequence of interest is single-stranded. If the target nucleic acid to be detected is a genomic sequence encoding a rRNA, then that target will naturally occur in a double-stranded form. This is also the case with products of the polymerase chain reaction (PCR). These double-stranded targets are naturally inhibitory to hybridization with a probe. Finally, undesirable intramolecular and intermolecular hybrids can form within a single probe molecule or between different probe molecules if there is sufficient self-complementarity. Thus, extensive self-complementarity in a probe sequence should be avoided.

Preferably, probes useful for carrying out the procedures described below will hybridize only under conditions of high stringency. Under these conditions only highly complementary nucleic acid hybrids will form (i.e., those having at least 14 out of 17 bases in a contiguous series of bases being complementary). Hybrids will not form in the absence of a sufficient degree of complementarity. Accordingly, the stringency of the assay conditions determines the amount of complementarity needed between two nucleic acid strands forming a hybrid. Stringency is chosen to maximize the difference in stability between the hybrid formed with the target and non-target nucleic acid. Exemplary high stringency conditions are employed in the Examples presented below.

While oligonucleotide probes of different lengths and base composition may be used for detecting Enterobacteriaceae, preferred probes in this invention have lengths of up to 100 nucleotides, and more preferably of up to 60 nucleotides. Preferred length ranges for the invented oligonucleotides are from 10 to 100 bases in length, or more preferably between 15 and 50 bases in length and are sufficiently homologous to the target nucleic acid to permit hybridization under high stringency conditions, such as those employed in the Examples described below. However, the specific probe sequences described below also may be provided in a nucleic acid cloning vector, transcript or other longer nucleic acid and still can be used for detecting members of the family Enterobacteriaceae.

Chemical Structure of Oligonucleotides

All of the oligonucleotides of the present invention may be modified with chemical groups to enhance their performance. Thus, it is to be understood that references to "oligonucleotide probes" or "helper oligonucleotides" or simply "oligonucleotides" embrace polymers of native nucleotides as well as polymers that include at least one nucleotide analog.

Backbone-modified oligonucleotides, such as those having phosphorothioate or methylphosphonate groups, are examples of analogs that can be used in conjunction with oligonucleotides of the present invention. These modifications render the oligonucleotides resistant to the nucleolytic activity of certain polymerases or to nuclease enzymes. Other analogs that can be incorporated into the structures of the oligonucleotides disclosed herein include peptide nucleic acids, or "PNAs." The PNAs are compounds comprising ligands linked to a peptide backbone rather than to a phosphodiester backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker. The PNAs are able to bind complementary ssDNA and RNA strands. Methods for making and using PNAs are disclosed in U.S. Pat. No. 5,539,082. Another type of modification that can be used to make oligonucleotides having the sequences described herein involves the use of non-nucleotide linkers (e.g., Arnold, et al., "Non-Nucleotide Linking Reagents for Nucleotide Probes", U.S. Pat. No. 6,031,091 hereby incorporated by reference) incorporated between nucleotides in the nucleic acid chain which do not interfere with hybridization or the elongation of a primer.

Nucleic Acid Based Methods of Detecting rRNA or rDNA

A composition that includes an oligonucleotide probe, either alone or in combination with one or more helper oligonucleotides, can be used for detecting rRNA or rDNA of bacteria within the family Enterobacteriaceae in a hybridization assay. Defined oligonucleotides that can be used to practice the present invention can be produced by any of several well-known methods, including automated solid-phase chemical synthesis using cyanoethylphosphoramidite precursors (Barone et al., *Nucl Acids Res* 12:4051 (1984)). Other well-known methods for preparing synthetic oligonucleotides also may be employed.

Essentially any labeling and detection system that can be used for monitoring specific nucleic acid hybridization can be used in conjunction with the probes disclosed herein when a labeled probe is desired. Included among the collection of useful labels are: isotopic labels, enzymes, haptens, linked oligonucleotides, chemiluminescent molecules and redox-active moieties that are amenable to electrochemical detection methods. Standard isotopic labels that can be used to produce labeled oligonucleotides include $^3$H, $^{35}$S, $^{32}$P, $^{125}$I, $^{57}$Co and $^{14}$C. When using radiolabeled probes, hybrids can be detected by autoradiography, scintillation counting or gamma counting.

Non-isotopic materials can also be used for labeling oligonucleotide probes. These non-isotopic labels can be positioned internally or at a terminus of the oligonucleotide probe. Modified nucleotides may be incorporated enzymatically or chemically with modifications of the probe being performed during or after probe synthesis, for example, by the use of non-nucleotide linker groups. Non-isotopic labels include fluorescent molecules, chemiluminescent molecules, enzymes, cofactors, enzyme substrates, haptens or other ligands. Acridinium esters are particularly preferred non-isotopic labels useful for detecting probe hybrids.

Indeed, any number of different non-isotopic labels can be used for preparing labeled oligonucleotides in accordance with the invention. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. U.S. Pat. No. 5,998,135 discloses yet another method that can be used for labeling and detecting the probes of the present invention using fluorimetry to detect fluorescence emission from lanthanide metal labels disposed on probes, where the emission from these labels becomes enhanced when it is in close proximity to an energy transfer partner. Preferred electrochemical labeling and detection approaches are disclosed in U.S. Pat. Nos. 5,591,578 and 5,770,369, and the published International Patent Application No. PCT/US98/12082, the disclosures of which are hereby incorporated by reference. Redox active moieties useful as electrochemical labels in the present invention include transition metals such as Cd, Mg, Cu, Co, Pd, Zn, Fe and Ru.

Those having an ordinary level of skill in the art will appreciate that alternative procedures for detecting nucleic acids of bacteria in the family Enterobacteriaceae using the invented probes can be carried out using either labeled probes or unlabeled probes. For example, hybridization assay methods that do not rely on the use of a labeled probe are disclosed in U.S. Pat. No. 5,945,286 which describes immobilization of unlabeled probes made of peptide nucleic acids (PNAs), and detectably labeled intercalating molecules which can bind double-stranded PNA probe/target nucleic acid duplexes. In these procedures, as well as in certain electrochemical detection procedures, such as those disclosed in published International Patent Application No. PCT/US98/12082 entitled "Detection of Analytes Using Reorganization Energy," published International Patent Application No. PCT/US98/12430 entitled "Electronic Methods for the Detection of Analytes," and in published International Patent Application No. PCT/US97/20014 entitled "Electrodes Linked Via Conductive Oligomers to Nucleic Acids" the oligonucleotide probe is not required to harbor a detectable label.

Acceptability of the final product following synthesis and purification of an oligonucleotide may be verified by any of several procedures. First, polyacrylamide gel electrophoresis can be used to determine the size and purity of the oligonucleotide according to standard laboratory methods (see *Molecular Cloning: A Laboratory Manual,* Sambrook et al., eds. Cold Spring Harbor Lab Publ., 11.51, (1989)). Alternatively, High Pressure Liquid Chromatography ("HPLC") procedures can be used for this same purpose.

Hybridization between the labeled oligonucleotide probe and target nucleic acid in the procedures described below can be enhanced through the use of unlabeled "helper oligonucleotides" according to the procedure disclosed by Hogan et al., in U.S. Pat. No. 5,030,557 entitled, "Means and Methods for Enhancing Nucleic Acid Hybridization." As indicated above, helper oligonucleotides bind a region of the target nucleic acid other than the region that is bound by the assay probe. This binding imposes new secondary and tertiary structures on the targeted region of the single-stranded nucleic acid and accelerates the rate of probe binding. Helper oligonucleotides which can be used in combination with labeled oligonucleotide probes of the present invention are preferably 17 to 100 nucleotides in length and have a sequence that includes at least 17 contiguous nucleotides contained within the sequence of SEQ ID NO:10. Other preferred Helper oligonucleotides have lengths of up to 100 nucleotides and include at least 24 contiguous nucleotides, or more preferably 41 contiguous nucleotides contained within the sequence of SEQ ID NO:10.

Those having an ordinary level of skill in the art will appreciate that factors affecting the thermal stability of a probe:target hybrid also can influence probe specificity. Accordingly, the melting profile, including the melting temperature (Tm) of probe:target hybrids, should be empirically determined for each probe:target combination. A preferred method for making this determination is described by Arnold et al., in U.S. Pat. No. 5,283,174, entitled "Homogeneous Protection Assay."

One approach for measuring the Tm of a probe:target hybrid involves conducting a hybridization protection assay. According to the method of this assay, a probe:target hybrid is formed under conditions of target excess in a lithium succinate buffered solution containing lithium lauryl sulfate. Aliquots of the "preformed" hybrids are diluted in the hybridization buffer and incubated for five minutes at various temperatures starting below the anticipated Tm (typically 55° C.) and increasing in 2–5 degree increments. This solution is then diluted with a mildly alkaline borate buffer and incubated at a lower temperature (for example 50° C.) for ten minutes. An acridinium ester (AE) linked to a single-stranded probe will be hydrolyzed under these conditions while an acridinium ester linked to a hybridized probe will be relatively "protected." This procedure is referred to as the hybridization protection assay ("HPA"). The amount of chemiluminescence remaining is proportional to the amount of hybrid and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In an alternative approach, the Tm of a probe:target hybrid can be determined using an isotopically labeled probe. In all cases, the Tm for a given hybrid will vary depending on the concentration of salts, detergents and other solutes contained in the hybridization solution. All of these factors influence relative hybrid stability during thermal denaturation (*Molecular Cloning: A Laboratory Manual* Sambrook et al., eds. Cold Spring Harbor Lab Publ., 9.51 (1989)).

The rate at which a probe hybridizes to its target is a measure of the thermal stability of the target secondary structure in the probe region, and can be can be determined using $C_0t_{1/2}$ measurements. These kinetic measurements of hybridization rate have units of (moles of nucleotide per liter)×(seconds). Expressed more simply, the $C_0t_{1/2}$ value is the concentration of probe times the half-life of hybridization at that concentration. This value can be determined by hybridizing various amounts of probe to a constant amount of target nucleic acid for a fixed time. For example, 0.05 pmol of target is incubated with 0.012, 0.025, 0.05, 0.1 and 0.2 pmol of probe for 30 minutes. The $C_0t_{1/2}$ may also be determined by hybridizing the target and probe under conditions of target excess and then measuring the increase in duplex formation over time. The amount of hybrid present can be measured using the above-described HPA procedure or by scintillation counting if a radiolabeled probe is used in the procedure. When using the HPA procedure, the measured signal is then plotted as the log of the percent of maximum Relative Light Units ("RLU") from the highest probe concentration versus probe concentration (moles of nucleotide per liter). The $C_0t_{1/2}$ is graphically determined from the concentration corresponding to 50% of maximum hybridization multiplied by the hybridization time in seconds. These values range from $9 \times 10^{-6}$ to $9 \times 10^{-5}$ with the preferred values being less than $3.5 \times 10^{-5}$. Similar values may be obtained by measuring radioactivity and plotting % hybridization at a given time point vs maximum hybridization extent.

In a preferred method of determining whether a biological sample contains rRNA or rDNA that would indicate the presence of Enterobacteriaceae, nucleic acids can be released from cells by sonic disruption, for example according to the method disclosed by Murphy et al., in U.S. Pat. No. 5,374,522. Other known methods for disrupting cells include the use of enzymes, osmotic shock, chemical treatment, and vortexing with glass beads. Other methods suitable for liberating from microorganisms the nucleic acids that can be subjected to the hybridization methods disclosed herein have been described by Clark et al., in U.S. Pat. No. 5,837,452 and by Kacian et al., in U.S. Pat. No. 5,364,763. Following or concurrent with the release of rRNA, labeled probe may be added in the presence of accelerating agents and incubated at the optimal hybridization temperature for a period of time necessary to achieve significant hybridization reaction.

The following polynucleotide sequence was characterized by the criteria of length, Tm and nucleotide sequence and was found to be specific for the rRNA of E. coli and other members of the family Enterobacteriaceae: EntA1263 CCGCTTGCTCTCGCGAG (SEQ ID NO:1). This sequence is complementary to a unique segment found in the 16S rRNA of E. coli and other members of the family Enterobacteriaceae. A representative list of bacteria in the family Enterobacteriaceae can be found in Table 2. The probe is 17 bases in length and hybridized rRNA of E. coli and other Enterobacteriaceae in a region corresponding to bases 1263–1279 of the E. coli 16S rRNA.

This probe is one illustration of an oligonucleotide that: (1) hybridizes the target nucleic acid under high stringency hybridization conditions, (2) has a length of up to 100 nucleotide bases, and (3) includes at least 17 contiguous nucleotides falling within the 1222–1303 target region identified by SEQ ID NO:10 or its complement. Other oligonucleotides having these properties are contemplated for use as hybridization assay detection probes and are embraced by the invention.

Similarly, oligonucleotides having the sequences of SEQ ID NOs:2 and 3 are disclosed herein as illustrations of useful helper oligonucleotides. Like the helper oligonucleotides employed in the working Examples herein, other helper oligonucleotides embraced by the invention also have sequences of up to 100 nucleotides in length and further have at least 17 contiguous nucleotides contained within the target region identified by SEQ ID NO:10 or its complement.

As indicated below, the EntA1263 probe hybridized rRNA from E. coli and other members of the family Enterobacteriaceae in a manner that was promoted by the presence of helper oligonucleotides. According to the procedure used to make this determination, single-stranded probe oligonucleotide radiolabeled at the 5'-end was contacted with rRNA from E. coli in the presence or absence of helper oligonucleotides. Probe molecules hybridizing the rRNA to form double-stranded hybrids were separated from single-stranded probe molecules by hydroxyapatite capture. The double-stranded hybrids bound to the hydroxyapatite and were detected and quantitated by scintillation counting. The extent of hybridization was then calculated as a percentage. As indicated below, the Tm of the probe:target hybrid advantageously was increased in the presence of one or more helper oligonucleotides.

The following Example describes the methods used to demonstrate that the EntA1263 probe hybridized rRNA from E. coli, and that this interaction was facilitated by including helper oligonucleotides in the hybridization mixture.

EXAMPLE 1

Tm Determination for Probe:Target Hybrids

Tm values for probe:target and helper:target hybrids were determined using an end-labeled probe having the sequence of EntA1263 CCGCTTGCTCTCGCGAG (SEQ ID NO:1) and end-labeled helper oligonucleotides selected from the group: (A) EntA1222, GTCGCTTCTCTTTGTATGCGC-CATTGTAGCACGTGTGTAGC (SEQ ID NO:2), and (B) OMeEntA1280, GGACUACGACGCACUUUAUGAGGU (SEQ ID NO:3). Helpers A and B were selected to bind the rRNA of the Enterobacteriaceae in regions of the molecule immediately adjacent to the probe binding site, helper A binding in about the 1222–1262 region of the 16S rRNA, helper B binding in the 1280–1303 region of the 16S rRNA. The probe and helper oligonucleotides were 5'-end labeled using $[\gamma-^{32}P]ATP$ as a phosphate donor and T4 polynucleotide kinase to catalyze the phosphate transfer reaction essentially as described in *Molecular Cloning: A Laboratory Manual* (Sambrook et al., eds. Cold Spring Harbor Lab Publ. 10.59 (1989)). End-labeled oligonucleotides were separately combined with purified rRNA from E. coli to provide conditions of target excess. In trials that included both the probe and helper oligonucleotides, only the probe was end-labeled and each helper oligonucleotide was present in a 10 fold molar excess over the target. All mixtures were hybridized to completion in a solution that included 0.48 M sodium phosphate buffer, 0.1% sodium dodecyl sulfate, 1 mM EDTA and 1 mM EGTA. As negative controls, the probe and/or helper oligonucleotides were hybridized in the absence of the nucleic acid target. At the conclusion of the hybridization procedure, mixtures were diluted and passed over a hydroxyapatite column to separate single-stranded nucleic acids from double-stranded hybrids. The amount of radioactivity in the column flow-through represented single-stranded probe and was measured by scintillation counting. The amount of radioactivity bound to the hydroxyapatite was separately measured by scintillation counting. The extent of hybrid formation, expressed as a percentage, was calculated by dividing the amount of probe (measured in cpm) bound to the hydroxyapatite by the total amount of probe (in cpm) that was applied to the column. Results of these procedures are presented in Table 1.

TABLE 1

Hybridization of an Enterobacteriaceae-Specific Probe with Target rRNA

|  | % Hybridization | Tm (° C.) |
| --- | --- | --- |
| EntA1263 Probe | 37.3 | 64 |
| helper A (EntA1222) | 97 | 77 |
| helper B (OMe EntA1280) | 100 | 80 |
| Probe + helper A | 92.4 | 67.2 |
| Probe + helper B | 91.5 | 68.2 |
| Probe + helper A + helper B | 97.3 | 73 |

The results from this procedure confirmed that the end-labeled probe hybridized E. coli rRNA and that this interaction advantageously was facilitated by helper oligonucleotides. We particularly observed that the Tm of the probe:target complex could be increased when helper oligonucleotides were included in the hybridization reaction. Although the probe can be used either alone or in combination with one or more helper oligonucleotides for hybridizing the rRNA of E. coli and Enterobacteriaceae, the below-described experiments to characterize the probe were conducted using the probe in combination with helper oligonucleotides having the sequences of EntA1222 and OMeEntA1280. Combinations of probes and helper oligonucleotides useful in the procedures described herein preferably have probe:target Tm values in the range of 64–73° C. under the conditions described above.

Probe specificity was confirmed by demonstrating positive hybridization to rRNAs from a specificity panel. The collection of organisms used as sources of target nucleic acids in this procedure represented a broad taxonomic cross-section of organisms and a nearest-neighbor group. In the following procedure, quantitative results using the AE-labeled hybridization probe were compared to the amount of bacterial rRNA present in each sample using a positive control probe. This positive control probe, which hybridized rRNA from all species of bacteria, was particularly useful for confirming the presence of bacterial rRNA in samples that failed to hybridize the EntA1263 probe. In such an event, the positive control probe provided confirmation for the presence of hybridizable rRNA and so validated the negative results. In the case of fungal rRNA targets, a broadly reactive fungal rRNA hybridization probe served as the positive control.

The following Example describes the methods used to demonstrate that the EntA1263 probe hybridized rRNAs from a panel of Enterobacteriaceae.

EXAMPLE 2

Verification of Probe Specificity

Bacterial lysates or purified RNA were used as nucleic acid targets for hybridization of a probe having the sequence of EntA1263 together with helper oligonucleotides having the sequences of EntA1222 and OMeEntA1280. Organisms employed as sources of rRNA in this procedure were either typed clinical isolates or obtained from the American Type Culture Collection (ATCC). All samples are identified in Table 2 by name and by master log numbers of Gen-Probe Incorporated. Parallel samples of each rRNA were hybridized with a labeled positive control probe (OMeEcoB1933) having the sequence CGACAAGGAAUUUCGC (SEQ ID NO:4) and a first unlabeled helper oligonucleotide (OMeEcoB1916) having the sequence UACCUUAGGAC-CGUUAU (SEQ ID NO:5) and a second unlabeled helper oligonucleotide (OMeEcoB1949a) having the sequence CAGGUCGGAACUUACC (SEQ ID NO:6). The hybridization solution contained 0.6 M LiCl, 1% lithium lauryl sulfate, 60 mM lithium succinate and 10 mM of both EDTA and EGTA, pH 5.5. Both the EntA1263 probe and the positive control probe were labeled with acridinium ester essentially according to the method disclosed in U.S. Pat. No. 5,185,439, entitled "Acridinium Ester Labeling and Purification of Nucleotide Probes." At the conclusion of the hybridization reaction, acridinium ester linked to unhybridized probe was rendered non-chemiluminescent under mild alkaline conditions, while acridinium ester attached to hybridized probe remained resistant to the inactivation. Conditions for the hydrolysis and detection of hybridized probe labeled with acridinium ester are described by Arnold et al., in *Clin. Chem.* 35:1588 (1989)). The magnitudes of probe hybridization in these procedures were quantitated by luminometry using procedures familiar to those having ordinary skill in the art. The magnitude of the Enterobacteriaceae probe signal was then divided by the magnitude of the bacterial positive control signal to quantitatively normalize results in the study. Samples having Enterobacteriaceae probe signals that were greater than 15% of the positive control signal indicated specific hybridization with the EntA1263 AE probe, while lower values indicated negative results for this assay format. Quantitative results of the assay are shown in Table 2.

TABLE 2

Hybridization of the EntA1263 Probe and rRNA-Containing Lysates from a Collection of Enterobacteriaceae

| | | Hybridization Results | | |
|---|---|---|---|---|
| GP#* | rRNA Source | Pan-Bacterial Probe (RLU) | Enterobacteriaceae Probe (RLU) | Fractional Hybridization (%) |
| #152 | Citrobacter diversus | 6126 | 13290 | 217 |
| #150 | Citrobacter freundii | 8479 | 18614 | 220 |
| #153 | Enterobacter aerogenes | 7597 | 15213 | 200 |
| #154 | Enterobacter agglomerans | 8044 | 13038 | 162 |
| #155 | Enterobacter cloacae | 7441 | 14067 | 189 |
| #215 | Enterobacter fragilis | 6467 | 14466 | 224 |
| #156 | Enterobacter gergoviae | 2729 | 6909 | 253 |
| #159 | Escherichia coli | 5141 | 9991 | 194 |
| #161 | Escherichia fergusonii | 4152 | 7989 | 192 |
| #162 | Escherichia hermanii | 2821 | 6309 | 224 |
| #188 | Hafnia alvei | 47098 | 109965 | 233 |
| #163 | Klebsiella oxytoca | 2642 | 5720 | 217 |
| #164 | Klebsiella ozaenae | 4806 | 11341 | 236 |
| #176 | Klebsiella pneumoniae | 4185 | 7265 | 174 |
| #178 | Klebsiella rhinoscleromatis | 3121 | 5859 | 188 |
| #179 | Proteus mirabilis | 4669 | 9647 | 207 |
| #183 | Proteus penneri | 3607 | 22675 | 629 |
| #181 | Proteus vulgaris | 5621 | 20266 | 361 |
| #186 | Providencia alcalifaciens | 43548 | 116515 | 268 |
| #187 | Providencia rettgeri | 30678 | 66745 | 218 |
| #185 | Providencia stuartii | 13480 | 20248 | 150 |
| #189 | Salmonella enteritidis | 20228 | 49095 | 243 |
| #216 | Salmonella paratyphi | 3822 | 8867 | 232 |
| #165 | Salmonella typhi | 7326 | 16866 | 230 |
| #166 | Salmonella typhimurium | 5119 | 11626 | 227 |

TABLE 2-continued

Hybridization of the EntA1263 Probe and rRNA-Containing Lysates from a Collection of Enterobacteriaceae

| | | Hybridization Results | | |
|---|---|---|---|---|
| GP#* | rRNA Source | Pan-Bacterial Probe (RLU) | Enterobacteriaceae Probe (RLU) | Fractional Hybridization (%) |
| #170 | Serratia liquefaciens | 5355 | 15447 | 288 |
| #171 | Serratia marcescens | 4647 | 9934 | 214 |
| #168 | Shigella dysenteriae | 4787 | 11103 | 232 |
| #169 | Shigella sonnei | 4675 | 11115 | 238 |
| #173 | Yersinia enterocolitica | 5719 | 9899 | 173 |
| #175 | Yersinia intermedia | 4800 | 9204 | 192 |
| #174 | Yersinia pseudotuberculosis | 5118 | 3113 | 61 |
| #184 | Morganella morganii | 3406 | 292 | 9 |

*"GP" entries indicate master log numbers for Gen-Probe Incorporated.

The results presented in Table 2 confirmed that the probe directed against Enterobacteriaceae rRNA efficiently hybridized rRNA samples from numerous Enterobacteriaceae species. Significantly, the probe did not substantially hybridize to rRNA of *Morganella morganii*. It is to be understood that the 16S rRNA of this organism includes several mismatched nucleotide positions with respect to the probe. Interestingly, the art field appreciates that classification of this organism has been somewhat uncertain, a fact that is reflected by numerous name changes in the past.

Specificity of the probe directed against Enterobacteriaceae was further investigated by hybridizing the labeled probe with a series of rRNA species representing a broad spectrum of phylogenetically diverse organisms. In this procedure, AE-labeled probe was separately mixed with individual rRNA-containing lysates or purified rRNA from organisms that were phylogenetically unrelated to the Enterobacteriaceae. Positive hybridization results obtained using the positive control probe and negative results obtained using the EntA1263 probe in the following procedure further indicated that the probe advantageously was highly specific for organisms in the family Enterobacteriaceae.

The following Example describes additional methods used to demonstrate specificity of the probe. More particularly, the following procedures showed that the EntA1263 probe did not cross hybridize with rRNAs from non-Enterobacteriaceae organisms.

EXAMPLE 3

Absence of Cross Hybridization with Unrelated rRNAs

Hybridization assays were conducted using the AE-labeled probes and helper oligonucleotides according to the procedures described in the previous Example except that lysates containing rRNAs or purified rRNAs from numerous phylogenetically diverse bacteria or 20 fungal organisms served as target nucleic acids. A pan-fungal probe having the sequence GTCTGGACCTGGTGAGTTTCCC (SEQ ID NO:7), and helper oligonucleotides having the sequences CGUGUUGAGUCAAAUUAAGCCGC (SEQ ID NO:8) and GCUCUCAAUCUGUCAAUCCUUA-UUGU (SEQ ID NO:9) were used as positive controls to detect fungal rRNAs. Results of the procedure are presented in Tables 3 and 4.

TABLE 3

Hybridization of an Enterobacteriaceae-Specific Probe with rRNA from a Collection of Phylogenetically Related Organisms

| | | Hybridization Results | | |
|---|---|---|---|---|
| GP# | rRNA Source | All Bacterial Probe (RLU) | Enterobacteriaceae Probe (RLU) | Fractional Hybridization (%) |
| #234 | Acinetobacter calcoaceticus | 3784 | 103 | 3 |
| #233 | Acinetobacter lwoffi | 3914 | 97 | 2 |
| #13 | Bacillus brevis | 8615 | 136 | 2 |
| #11 | Bacillus subtilis | 4506 | 170 | 4 |
| #212 | Bacteriodes fragilis | 7165 | 74 | 1 |
| #226 | Bacteroides ovatus | 3676 | 47 | 1 |
| #225 | Bacteroides thetaiotamicron | 32979 | 10 | 0 |
| #192 | Clostridium perfringens | 7144 | 185 | 3 |
| #236 | Corynebacterium aquaticum | 19019 | 58 | 0 |
| #239 | Corynebacterium jeikieum | 8827 | 7 | 0 |
| #237 | Corynebacterium xerosis | 8776 | 0 | 0 |
| #46 | Enterococcus avium | 9135 | 635 | 7 |
| #27 | Enterococcus casseliflavus | 9661 | 208 | 2 |
| #7 | Enterococcus cecorum | 5233 | 132 | 3 |
| #15 | Enterococcus dispar | 8492 | 123 | 1 |
| #85 | Enterococcus durans | 8130 | 48 | 1 |
| #82 | Enterococcus faecalis | 7201 | 39 | 1 |
| #79 | Enterococcus faecium | 6987 | 34 | 0 |

TABLE 3-continued

Hybridization of an Enterobacteriaceae-Specific Probe with rRNA from a Collection of Phylogenetically Related Organisms

| | | Hybridization Results | | |
|---|---|---|---|---|
| GP# | rRNA Source | All Bacterial Probe (RLU) | Enterobacteriaceae Probe (RLU) | Fractional Hybridization (%) |
| #23 | Enterococcus faecium V1 | 4929 | 71 | 1 |
| #17 | Enterococcus faecium V6 | 5083 | 44 | 1 |
| #89 | Enterococcus gallinarum | 7973 | 0 | 0 |
| #81 | Enterococcus hirae | 5429 | 62 | 1 |
| #45 | Enterococcus malodoratus | 14729 | 165 | 1 |
| #25 | Enterococcus mundtii | 8804 | 161 | 2 |
| #26 | Enterococcus pseudoavium | 9364 | 48 | 1 |
| #33 | Enterococcus raffinosus | 5984 | 29 | 0 |
| #47 | Enterococcus sacchrolyticus | 8339 | 25 | 0 |
| #217 | Haemophilus influenzae | 3726 | 87 | 2 |
| #219 | Haemophilus influenzae A | 3751 | 57 | 2 |
| #220 | Haemophilus influenzae B | 3816 | 20 | 1 |
| #222 | Haemophilus parainfluenzae | 24669 | 26 | 0 |
| #36 | Lactobacillus acidophilus | 20052 | 100 | 0 |
| #56 | Lactobacillus jensenii | 5863 | 68 | 1 |
| #9 | Lactococcus lactis | 36172 | 152 | 0 |
| #41 | Listeria grayi | 2278 | 226 | 10 |
| #72 | Listeria ivanovii | 5646 | 79 | 1 |
| #31 | Listeria monocytogenes ½b | 9424 | 41 | 0 |
| #28 | Listeria monocytogenes 4b | 7547 | 86 | 1 |
| #73 | Listeria seeligeri | 6292 | 97 | 2 |
| #40 | Listeria welshimeri | 4610 | 230 | 5 |
| #240 | Micrococcus luteus | 1712 | 178 | 10 |
| #196 | Neisseria gonorrhoea | 6152 | 54 | 1 |
| #198 | Neisseria meningitidis | 19758 | 70 | 0 |
| #191 | Peptostreptococcs anaerobius | 6313 | 362 | 6 |
| #190 | Propionibacterium acnes | 5008 | 91 | 2 |
| #200 | Pseudomonas aeruginosa | 5099 | 102 | 2 |
| #203 | Pseudomonas cepacia | 24918 | 94 | 0 |
| #205 | Pseudomonas fluorescens | 8004 | 127 | 2 |
| #206 | Pseudomonas maltophilia | 7031 | 233 | 3 |
| #209 | Pseudomonas mendocina | 17308 | 112 | 1 |
| #208 | Pseudomonas pickettii | 7282 | 271 | 4 |
| #210 | Pseudomonas putida A | 7544 | 204 | 3 |
| #211 | Pseudomonas stutzeri | 7100 | 0 | 0 |
| #49 | Staphylococcus aureus | 5286 | 71 | 1 |
| #63 | Staphylococcus cohnii | 5544 | 124 | 2 |
| #6 | Staphylococcus delphini | 5917 | 116 | 2 |
| #50 | Staphylococcus epidermidis | 7754 | 88 | 1 |
| #62 | Staphylococcus haemolyticus | 4645 | 155 | 3 |
| #61 | Staphylococcus hominis | 4884 | 165 | 3 |
| #69 | Staphylococcus hyicus | 5484 | 105 | 2 |
| #60 | Staphylococcus intermedius | 6823 | 101 | 1 |
| #59 | Staphylococcus saprophyticus | 3484 | 88 | 3 |
| #39 | Staphylococcus simulans | 5890 | 371 | 6 |
| #67 | Staphylococcus warneri | 3565 | 129 | 4 |
| #53 | Streptococcus agalactiae | 6617 | 226 | 3 |
| #32 | Streptococcus agalactiae Ia | 9466 | 0 | 0 |
| #43 | Streptococcus anginosus | 8183 | 198 | 2 |
| #16 | Streptococcus avium | 5688 | 77 | 1 |
| #34 | Streptococcus bovis | 8620 | 47 | 1 |
| #51 | Streptococcus equi | 12255 | 190 | 2 |
| #80 | Streptococcus equinus | 4550 | 118 | 3 |
| #37 | Streptococcus equisimilis | 7445 | 116 | 2 |

*"GP#" entries indicate master log numbers for Gen-Probe Incorporated.

TABLE 4

Hybridization of the EntA1263 Probe with rRNA from a Collection of Fungal Organisms

| GP#* | ORGANISM | Pan-Bacterial Probe (RLU) | EntA1263 AE Probe (RLU) | Pan-Fungal Probe (RLU) | Hybrid (%) |
|---|---|---|---|---|---|
| F-932 | Arachnoitus flavoluteus | 481 | 293 | 232076 | 0.1 |
| F-906 | Aspergillus flavus | 364 | 140 | 348387 | 0.0 |
| F-899 | Aspergillus fumigatus | 382 | 225 | 419831 | 0.1 |
| F-907 | Aspergillus niger | 194 | 292 | 650747 | 0.0 |

TABLE 4-continued

Hybridization of the EntA1263 Probe with rRNA from a Collection of Fungal Organisms

| GP#* | ORGANISM | Pan-Bacterial Probe (RLU) | EntA1263 AE Probe (RLU) | Pan-Fungal Probe (RLU) | Hybrid (%) |
|---|---|---|---|---|---|
| F-930 | Auxarthron thaxteri | 301 | 209 | 494055 | 0.0 |
| F-1022 | Blastomyces dermatitidis | 296 | 200 | 422465 | 0.0 |
| 715 | Candida albicans | 369 | 212 | 327951 | 0.1 |
| 1123 | Candida glabrata | 1419 | 1512 | 45039 | 3.4 |
| 717 | Candida parapsillosis | 352 | 290 | 312482 | 0.1 |
| 1091 | Candida tropicalis | 1566 | 1255 | 24023 | 5.2 |
| F-1399 | Coccidioides immitis | 303 | 234 | 141956 | 0.2 |
| F-900 | Cryptococcus neoformans | 316 | 233 | 452943 | 0.1 |
| F-965 | Gymnoascus dugwayenis | 317 | 187 | 506033 | 0.0 |
| F-968 | Histoplasma capsulatum | 254 | 190 | 346283 | 0.1 |
| F-933 | Myxotrichum deflexum | 267 | 197 | 366688 | 0.1 |
| F-934 | Oidiodendron ecinulatum | 238 | 160 | 322685 | 0.0 |
| 716 | Candida krusei | 669 | 979 | 71371 | 1.4 |
| 1087 | Candida pseudotropicalis | 243 | 205 | 79868 | 0.3 |
| 384 | Saccharomyces cerevisiae | 116 | 120 | 75954 | 0.2 |
| 1080 | Candida guilliermondii | 320 | 322 | 65011 | 0.5 |

*"GP#" identifies fungal organisms by master log numbers for Gen-Probe Incorporated.

The results presented in Table 3 and Table 4 confirmed that the probe did not cross hybridize with the rRNAs from numerous phylogenetically diverse species. Taken together with the positive hybridization results presented in the Table 2, it was clear that the probe was highly specific for rRNA of the family Enterobacteriaceae.

The results presented above confirmed that the novel probes disclosed herein were capable of detecting Enterobacteriaceae. Moreover, the probes were capable of distinguishing Enterobacteriaceae from organisms that were phylogenetically related.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. An oligonucleotide 17 nucleotides in length, comprising a sequence selected from the group consisting of SEQ ID NO: 1 and the complement of SEQ ID NO: 1.

2. The oligonucleotide of claim 1, further comprising a detectable moiety.

3. The oligonucleotide of claim 2, wherein the detectable moiety is a chemiluminescent label or a radiolabel.

4. The oligonucleotide of claim 3, wherein the detectable moiety is a chemiluminescent label, and wherein the chemiluminescent label is an acridinium ester.

5. The oligonucleotide of claim 2, wherein said sequence is SEQ ID NO: 1.

6. A probe composition for detecting the 16S rRNA of bacteria in the family Enterobacteriaceae, comprising:
    an oligonucleotide probe 17 nucleotides in length and comprising the sequence of SEQ ID NO: 1.

7. The probe composition of claim 6, wherein said oligonucleotide probe further comprises a detectable moiety.

8. The probe composition of claim 7, further comprising at least one helper oligonucleotide.

9. The probe composition of claim 8, wherein said at least one helper oligonucleotide is selected from the group consisting of an oligonucleotide 41 nucleotides in length having the sequence of SEQ ID NO:2, and an oligonucleotide 24 nucleotides in length having the sequence of SEQ ID NO:3.

* * * * *